United States Patent [19]

Ogawa et al.

[11] Patent Number: 5,897,953
[45] Date of Patent: Apr. 27, 1999

[54] GRANULAR POLYMER COMPOSITE AND PRODUCTION PROCESS THEREOF AS WELL AS DIAGNOSTIC AGENT

[75] Inventors: Tetsuro Ogawa; Tsuneo Hiraide, both of Tokyo, Japan

[73] Assignee: Asahi Kogaku Kogyo Kabushiki Kaisha, Tokyo, Japan

[21] Appl. No.: 08/621,251

[22] Filed: Mar. 25, 1996

Related U.S. Application Data

[62] Division of application No. 08/318,089, Oct. 5, 1994, Pat. No. 5,540,995.

[30] Foreign Application Priority Data

Oct. 5, 1993 [JP] Japan .................................. 5-249506
Oct. 5, 1993 [JP] Japan .................................. 5-273016

[51] Int. Cl.$^6$ ............................ B32B 5/18; B32B 5/30; G01N 33/545
[52] U.S. Cl. .................. 428/407; 428/403; 436/531; 436/534
[58] Field of Search .................. 428/407, 403; 435/531, 534

[56] References Cited

U.S. PATENT DOCUMENTS

| | | |
|---|---|---|
| 3,802,997 | 4/1974 | Messing . |
| 4,804,624 | 2/1989 | Dorsett ........................ 435/5 |
| 4,837,168 | 6/1989 | de Jaeger et al. ............ 436/533 |
| 4,885,207 | 12/1989 | Johnson et al. ............... 428/403 |
| 5,030,391 | 7/1991 | Sumita et al. ................ 427/213.3 |
| 5,039,408 | 8/1991 | Ichitsuka et al. ............. 210/198 |
| 5,085,781 | 2/1992 | Tsuru et al. .................. 210/692 |
| 5,091,318 | 2/1992 | Anawis et al. ................ 436/513 |
| 5,231,035 | 7/1993 | Akers, Jr. ................... 436/531 |
| 5,273,908 | 12/1993 | Sakata et al. ................ 436/518 |
| 5,310,548 | 5/1994 | Tsuru et al. .................. 424/76.2 |
| 5,651,882 | 7/1997 | Ichitsuka et al. ............. 210/198 |

FOREIGN PATENT DOCUMENTS

| | | |
|---|---|---|
| 0325404 | 7/1989 | European Pat. Off. . |
| 3722102 | 1/1988 | Germany . |
| 63-16044 | 1/1988 | Japan . |
| 63-157973 | 6/1988 | Japan . |
| 1126554 | 5/1989 | Japan . |
| 3101608 | 4/1991 | Japan . |
| 3-254834 | 11/1991 | Japan . |
| 5-293372 | 11/1993 | Japan . |

OTHER PUBLICATIONS

English Translation of JP 1–126554.
English Translation of JP 3–101608.
DBA Abstract Accession No. 92–03556.
WPI Abstract Accession No. 89–088903/12.
WPI Abstract Accession No. 89–088902/12.
WPI Acc No. 88015425/03.
WPI Acc No. 93391878/49.
WPI Acc No. 92002534/01.
WPI Acc No. 88223663/A.
English Language Abstract of Japanese Patent Document 63–157973.
United Kingdom Search Report for GB application No. 9420131.6.
Tanaka et al., Powder Surface Modification Machine of High Speed Impact Method Nara Hybridization System and Application, Zairo Gijutsu (*Material Technology* Magazine), vol. 8, No. 8, Oct., 1990, pp. 274–286 and English Language abstract thereof.

*Primary Examiner*—Mary E. Ceperley
*Attorney, Agent, or Firm*—Greenblum & Bernstein P.L.C.

[57] ABSTRACT

A granular polymer composite comprising polymeric granules having coated on a surface thereof a calcium phosphate compound, at least a part of the particles of the calcium phosphate compound penetrates into the polymeric granules. The composite has a high bonding strength between the polymeric granules as a matrix and a coating of the calcium phosphate compound and also can fully exhibit the functions of a calcium phosphate compound. Using the granular polymer composite, a diagnostic agent which comprises of an antigen or antibody is adsorbed and immobilized on the composite and is therefore useful in diagnostic tests utilizing an antigen-antibody reaction for a number of infectious diseases.

12 Claims, 2 Drawing Sheets

& nbsp;
GRANULAR POLYMER COMPOSITE AND PRODUCTION PROCESS THEREOF AS WELL AS DIAGNOSTIC AGENT This application is a division of application Ser. No. 08/318,089, filed Oct. 05, 1994, now U.S. Pat. No. 5,540, 995.

BACKGROUND OF THE INVENTION

1. Field of the invention

The present invention relates to a granular polymer composite and a production process thereof as well as a diagnostic agent using the composite and a production process thereof. More particularly, the present invention relates to a granular polymer composite which is useful as an adsorbent, deodorizing agent, filler for a chromatographic column and others, and a production process of such polymer composites. The present invention also relates to a diagnostic agent using the polymer composite which is useful in the diagnostic procedures for a number of infectious diseases, and a production process of s uch types of diagnostic agents.

2. Description of the Related Art

Since they have a high adsorptivity of various substances such as viruses, bacteria, animal and plant cells, proteins, enzymes, nucleic acids, odor components and the like, calcium phosphate compounds, especially hydroxyapatite, are widely used as an adsorbent, deodorizing agent or filler for a chromatographic column, for example.

In medical or clinical practice, diagnostic procedures utilizing an antigen-antibody reaction including, for example, the gel-diffusion method, radioimmunoassay and precipitation tests have been well-known and have been widely used in the detection of various infectious diseases.

Further, in recent years, immobilization procedures in which an antigen or antibody is bonded to an inert carrier to prepare an immobilized antigen or antibody, and then the immobilized antigen or antibody is in contact with a specimen to be detected to evaluate an antigen-antibody reaction of the specimen have been reported in many papers. In these immobilization procedures, if viruses or bacteria are directly used, the carrier simultaneously used must be selected from a group of materials which do not damage or kill the viruses or bacteria immobilized on the carrier. A typical example of the carrier material widely used in prior art immobilization procedures is a gel of polyacrylamide which can undesirably damage the viruses or bacteria because of chemical substances such as monomers, polymerization initiators and the like contained in the gel.

Furthermore, some examples using polystyrene, latex or particulate carriers such as beads or microcapsules in the detection of antigen-antibody reaction have been reported in papers. However, use of such carriers involves problems to be solved with regard to a stable immobilization of antigens or antibodies as well as reproducibility and reliability of the detection.

SUMMARY OF THE INVENTION

One object of the present invention is to provide a composite containing a calcium phosphate compound in which a matrix and a coating of the calcium phosphate compound are strongly bonded with each other and accordingly which can exhibit the functions of the calcium phosphate compounds.

Another object of the present invention is to provide a process for the production of such composite body.

Still another object of the present invention is to provide a diagnostic agent which can effectively immobilize antigens such as viruses, bacteria and the like or the antibodies of the antigens onto the matrix thereof and accordingly which can be used in the antigen-antibody reaction with a high degree of sensitivity, reproducibility and reliability in the diagnostic procedures of infectious diseases.

Also, another object of the present invention is to provide a process for the production of such diagnostic agents.

The other objects of the present invention will be appreciated from the descriptions as set forth below with regard to the preferred embodiments thereof.

According to one aspect of the present invention, the above object can be attained by a granular polymer composite which comprises polymeric granules having been coated on their surface with a calcium phosphate compound, and wherein at least some of the particles of the calcium phosphate compound penetrates into the polymeric granules.

According to another aspect of the present invention, the above object can be attained by a process for the production of a granular polymer composite which comprises physically impinging particles of a calcium phosphate compound against polymeric granules to thereby form a coating of the calcium phosphate compound on the surface of the polymeric granules, and which in addition causes some of the particles of calcium phosphate to penetrate the polymeric granules.

According to still another aspect of the present invention, the above object can be attained by a diagnostic agent comprising a granular polymer composite which comprises polymeric granules having been coated on their surface with a calcium phosphate compound, the polymeric granules of the composite at least having been dyed; and an antigen or antibody adsorbed and immobilized on the composite, and wherein unadsorbed sites of said composite have been treated with a blocking agent.

According to still another aspect of the present invention, the above object can be attained by a process for the production of a diagnostic agent which comprises the steps of:

providing a granular polymer composite which comprises polymeric granules having been coated on their surface with a calcium phosphate compound, and wherein the polymeric granules of the composite have been dyed;

adsorbing and immobilizing an antigen or antibody on the composite; and treating the unadsorbed sites of the composite with a blocking agent.

The present disclosure relates to subject matter contained in the Japanese patent application Nos. 5-249506 and 05-273016 (both filed on Oct. 5, 1993) which are expressly incorporated herein by reference in their entirety.

DESCRIPTION OF THE PREFERRED EMBODIMENTS

Figure 1:
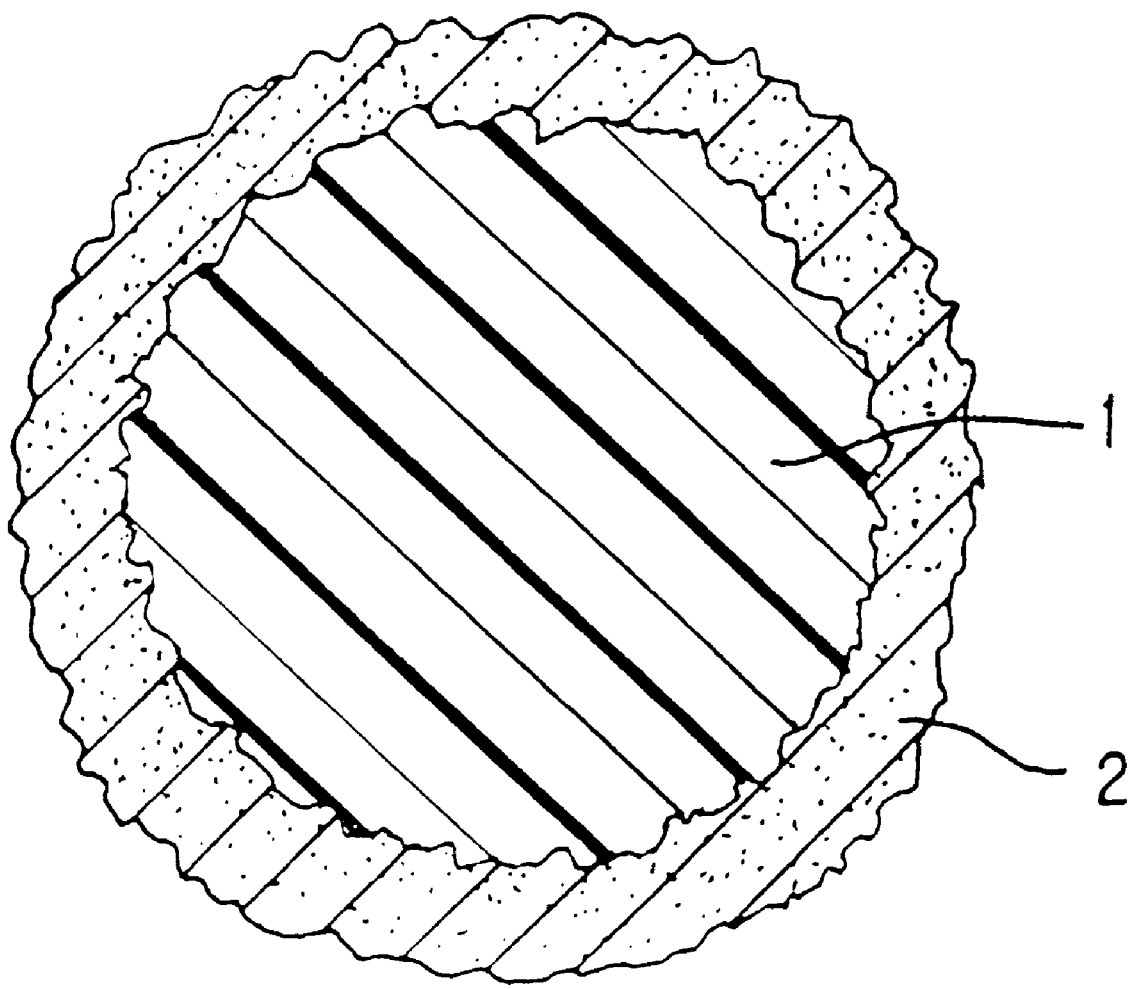
FIG. 1 is a cross-sectional view illustrating the cross-sectional structure of the polymeric composite according to the present invention.

The composite according to the present invention, as described above, includes of polymeric granules in the form of a matrix or carrier with the surface of the polymeric granules containing a coating of calcium phosphate compound. Preferably, the polymeric granules have allowed some of the calcium phosphate compound to penetrate into an inner portion of the granules. The coating of the polymeric granules with the calcium phosphate compound can be preferably carried out by physically impinging particles of the calcium phosphate compound against a surface of the polymeric granules at a high speed of impingement.

In the granular polymer composite according to the present invention, the polymers used as a matrix can be selected from a wide variety of well-known thermoplastic or thermosetting resins. Typical examples of useful thermoplastic resins include nylon (long-chain polyamide), polyethylene, polypropylene, polystyrene, acrylic resin, methacrylic resin (for example, polymethylmethacrylate), thermoplastic polyurethane and the like. Typical examples of useful thermosetting resins include phenolic resin, epoxy resin, melamine resin, urea resin, unsaturated polyester, alkyd resin, thermosetting polyurethane, ebonite and the like.

In the polymeric composite of the present invention, the above mentioned polymers are used in the form of granules. The size or diameter of the granules of the polymer used can be widely varied depending upon various factors such as the intended use of the composite, however, generally, it is preferred that the polymeric granules have an average granule diameter of 1 to 20 microns in the range of grain size distribution of $d_{75}/d_{25} \leq 2$. Note that $d_{25}$ means a granule size or diameter of the polymeric granules determined with regard to 25% of the cumulative undersieve granules, and $d_{75}$ means a granule size or diameter of the polymeric granules determined with regard to 75% of the cumulative undersieve granules. The average granule diameter of less than 1 micron results in a remarkably reduced penetration of the calcium phosphate compound into the polymeric granules, and the average granule diameter of more than 20 microns results in an undesirable formation of polymeric composite having varying densities.

Further, it is preferred that the polymeric granules used have a density of 0.9 to 1.2 $g/cm^3$. Assuming that the polymeric composite is used in a liquid, the polymeric granules should preferably have a density of 0.9 $g/cm^3$ or more in order to adjust the specific gravity of the composite to a value higher than that of water, and also they should preferably have a density of 1.2 $g/cm^3$ or less in order to satisfy the requirements for the physical impingement process and the practical use of the composite body.

As previously mentioned, the composite of granular polymers of the present invention is characterized in that a part of particles of the calcium phosphate compound has penetrated into the polymeric granules and thus forms a coated layer of the calcium phosphate compound around the polymeric granules.

The calcium phosphate compounds chosen should not adversely effect the resulting composite. Accordingly, the calcium phosphate compounds can be optionally selected from a wide variety of useful calcium phosphate compounds having a ratio of calcium and phosphorus (Ca/P) of 1.0 to 2.0. For example, one or more of $Ca_{10}(PO_4)_6(OH)_2$, $Ca_{10}(PO_4)_6F_2$, $Ca_{10}(PO_4)_6C_{12}$, $Ca_3(PO_4)_2$, $Ca_2P_2O_7$ and $Ca(PO_3)_2$ may be advantageously used as a calcium phosphate compound. Among these useful calcium phosphate compounds, the most preferred one is a calcium phosphate compound which contains hydroxyapatite as a principal component thereof. When fluoroapatite is used as a calcium phosphate compound, it is preferred that a content of fluorine in all the calcium phosphate compounds is less than 5% by weight, because the fluorine content above 5% by weight can exhibit an undesirable eluation of fluorine from the composite. The calcium phosphate compounds may be produced in any conventional manners including both a wet process and a dry process.

With regard to the calcium phosphate compounds used in the present invention, it is preferred that the particles thereof have an apparent density of 1.5 to 2.5 $g/cm^3$. The apparent density of less than 1.5 $g/cm^3$ results in the composites having a density lower than that of water, and the apparent density of more than 2.5 $g/cm^3$ causes a notable reduction of the adsorption characteristics in the composites. Note that the "apparent density" of the particles of the calcium phosphate compounds means an apparent density including water, i.e., a density of the particles applied when a Stokes diameter of the particles is determined in a water medium in a settling method, and is calculated from the following formula:

$$V\infty = g \cdot dp^2 (\rho_p - \rho)/18 \mu$$

in which $V\infty$ represents a settling terminal velocity, g represents a gravity, $\rho_p$ represents an apparent density (of particles)

dp represents a diameter of particles, $\rho$ represents a density of water, and $\mu$ represents a viscosity of water.

Furthermore, the particles of the calcium phosphate compounds are preferably porous particles of agglomerated primary particles having a specific surface area of not less than 10 $m^2/g$ and pore size of about 500 to 1000 angstroms. The specific surface area of less than 10 $m^2/g$ should be avoided, because such specific surface areas do not ensure a satisfactory adsorptivity. Also, in order to attain introduction of the adsorbed proteins and other substances into pores of the particles, it is preferred that the porous particles have pores having the above-mentioned pore size of about 500 to 1000 angstroms.

In the practice of the present invention, the porous particles of the calcium phosphate compounds can be produced in any conventional manner. For example, they can be produced from starting particles which are crystalline particles of the calcium phosphate compounds synthesized in a wet process. A slurry of the starting particles in the form of a suspension is directly spray-dried to form secondary particles or is indirectly spray-dried to form secondary particles, after the addition of a viscosity modifier (ie. the particles of an organic compound or fibers capable of being dissipated upon heating and the like to the slurry).

The resulting secondary particles have already a porous structure and accordingly they may be used as a starting material in the production of the polymeric composite, if desired. Alternatively, if it is desired to obtain porous particles of the calcium phosphate compounds having a high porosity, such porous granules can be produced by preparing a slurry of the resulting secondary particles as a suspension and then molding the slurry in a wet process or in a dry process under pressure to produce a block body of the calcium phosphate compounds. In the preparation of the slurry, any organic compound which can be dissipated from the block body during the subsequent sintering process may be added to the slurry in order to assist the formation of finely spaced pores in the resulting granules. Of course, the addition of such an organic compound is optional, and it may be omitted, because a pore size or diameter of the granules can be controlled by changing the applied sintering temperature and other conditions. The obtained block body is then sintered at a temperature of 500 to 1300° C. Note that a temperature of less than 500° C. is insufficient to complete thermal dissipation of the organic compound and sintering of the block body. And, if sintering of the block body is carried out at a temperature of greater than 1300° C., an excessively dense sintered body can be produced or a decomposition of the calcium phosphate can be caused. The thus sintered block body is pulverized and classified to obtain porous granules having the desired porosity. The pore size of the porous granules can be changed by suitably controlling the size of the crystalline particles of the calcium phosphate compounds in the starting slurry for use in the preparation of the secondary particles, the viscosity of the slurry, the particular choice of additives and other factors.

The granular composite according to the present invention can be produced in any conventional manner, and preferably, as previously mentioned, can be produced by physically impinging the particles of the calcium phosphate compound against the polymeric granules to thereby surface coat the polymeric granules with the calcium phosphate compound. The physical impingement of the calcium phosphate compound against the polymeric granules can be preferably carried out in a dry process by using conventional hybridization systems such as "Nara Hybridization System NHS-1" commercially available from Kabushikikaisha Nara Kikai Seisakusho and "HI-X200" commercially available from Nisshin Engineering KabushikiKaisha. Using these systems, generally, it is preferred that particles of the calcium phosphate compound and polymeric granules are blended to make a mixture having a weight ratio of 0.05 to 0.50 and the temperature of the mixture in the system is maintained at a temperature lower than the softening temperature of the polymer used, typically 80° C. or less.

It is preferred that the particles of the calcium phosphate compound have an average particle diameter of not more than 100 microns. Since the particles of the calcium phosphate compound may be broken or crushed by physical impingement, they may have a considerably increased diameter in comparison to that of the polymer granules. However, an average particle diameter of more than 100 microns should be avoided, because impingement speed of the particles is lowered, which makes it less likely for the particles to break, crush and penetrate into the polymer granules.

In the practice of the present invention, the calcium phosphate particles are not required to be introduced in a central or core portion of the polymeric granules upon physical impingement. Namely, with regard to the calcium phosphate particles, it is only required that at least a part of the particles penetrates the polymeric granules. This is because the polymeric granules can strongly grip and fix the calcium phosphate particles applied thereto, since the impinged calcium phosphate particulates are forced with the surrounding polymeric granules as a function of the elasticity of the polymeric granules.

FIG. 1 appended illustrates the formation of a coating 2 of the calcium phosphate compound over a surface of the polymeric granule 1. Preferably, a thickness of the calcium phosphate coating 2 is 0.1 to 5.0 microns. A coating thickness of less than 0.1 microns is insufficient to attain the desired adsorptivity. And, even if the coating thickness is increased to above 5.0 microns, the adsorptivity is not improved. Using the above-mentioned production process, the formation of a granular polymer composite in which the composite granules have an average granule diameter of 1.2 to 30.0 microns in the range of grain size distribution of $d_{75}/d_{25} \leq 2$, density of 1.05 to 1.35 g/cm$^3$ and pore size of 500 to 1000 angstroms and also a coating of the calcium phosphate compound has a layer thickness of 0.1 to 5.0 microns is contemplated. The polymeric composites are sufficient to accomplish a protein adsorption in the range of 0.2 to 4.0 mg of lysozyme per gram.

As can be appreciated from the above descriptions, according to the present invention, since the particles of the calcium phosphate compound penetrate into the polymeric granules, the calcium phosphate compound coating will not separate from the polymeric composites during handling and processing of the composites. It was found that the bonding strength between the calcium phosphate coating and the polymeric granules is so high that the calcium phosphate coating is still retained over the surface of the polymeric granules, even if a centrifugal force is applied to the composites. Further, since the polymeric material constitutes a core portion of the composites, an amount of the calcium phosphate compound which is relatively expensive to be used in the composites can be reduced and at the same time a large improvement in performance can be accomplished. Furthermore, since their surface contains a coating of the calcium phosphate compound, the polymeric composites of the present invention can be advantageously used in wide variety of fields, for example, they are useful as an adsorbent for viruses, bacteria, animal and plant cells, proteins, nucleic acids, enzymes and others, a deodorizer, a filler for chromatographic columns and the like.

The composite of granular polymers according to the present invention can exhibit an excellent adsorptivity to viruses, bacteria, proteins and others and accordingly, as previously mentioned, a novel and excellent diagnostic agent comprising the polymeric composite of the present invention having adsorbed thereon an antigen or antibody, and a production process thereof are provided.

The diagnostic agent according to the present invention is characterized in that a surface of the polymeric granules has a coating of a calcium phosphate compound, the polymeric granules of the composite or the whole composite is dyed; and an antigen or antibody is adsorbed and immobilized on the composite body, and that antigen-unadsorbed sites or antibody-unadsorbed sites of the composite are treated with a blocking agent.

In addition, the production process of a diagnostic agent according to the present invention is characterized by comprising the steps of:

providing a granular polymer composite which comprises polymeric granules having been coated on a surface with a calcium phosphate compound, the polymeric granules of the composite having at least been dyed;

adsorbing and immobilizing an antigen or antibody on the composite; and treating the unadsorbed sites of the composite with a blocking agent.

In the diagnostic agent and production process, the granular polymer composite is only required to have a coated surface of a calcium phosphate compound. It is preferred that the calcium phosphate compound is coated on the surface of the polymeric granules and at least a part of particles of the calcium phosphate compound penetrates into the polymeric granules.

Further, it is preferred that said composite granules have an average granule diameter of 1.2 to 30.0 microns in the range of grain size distribution of $d_{75}/d_{25} \leq 2$, density of 1.05 to 1.35 g/cm$^2$ and pore size of 500 to 1000 angstroms and a coating of the calcium phosphate compound has a layer thickness of 0.1 to 5.0 microns.

As is apparent from the above descriptions, the diagnostic agent of the present invention uses the specific polymeric composite as a carrier or matrix. Details of the polymeric composite used, including, for example, polymeric granules and particles of calcium phosphate compound used as starting materials, and the production process thereof will not be described hereinafter in order to avoid duplication of the description, because they have been already explained in detail prior to this description of the diagnostic agent.

The polymeric composite used in the diagnostic agent of the present invention can be dyed with any dye. It is preferred that at least the polymeric granules are dyed. Preferably, the dyed composite can be prepared by using the dyed polymeric granules as a starting material or alternatively by dyeing the composite after production thereof. In any cases, a suitable dye can be optionally selected from a wide variety of dyes such as direct dyes, acid dyes, basic dyes, mordant dyes, acidic mordant dyes, sulfur dyes, sulfur vat dyes, vat dyes, soluble vat dyes, azoic dyes, disperse dyes, reactive dyes, oxidation dyes, dyes for synthetic fibers, and fluorescent brightening dyes. Any pigment may be used in place of the dye material, if appropriate, dyeing may be carried out using any well-known dyeing method.

Since it contains a surface coating of the calcium phosphate compound, the dyed polymeric composite has an excellent adsorption of antigens and antibodies such as viruses, bacteria and the like, and therefore the dyed composite is suitable to provide an immobilized composite by adsorbing and immobilizing an antigen or antibody on the composite.

Any conventional immobilizing agents can be advantageously used in the above immobilization process. Typical examples of suitable immobilizing agent include glutaraldehyde and the like as a crosslinking agent, formaldehyde, silane coupling agent and the like as a binding agent or osmium tetrachloride. Examples of useful silane coupling agent include:
3-glycidoxypropyltrimethoxysilane,
3-thiopropyltrimethoxysilane,
2-(3-trimethoxysilylpropyldithio)-5-nitropyridine,
3-aminopropyltriethoxysilane,
3-chloropropyldimethoxymethylsilane and the like.

After immobilization, the antigen-unadsorbed sites or antibody-unadsorbed sites of the dyed composite are treated with a blocking agent. The blocking agent used herein is selected from those which are able to be adsorbed by any of the unadsorbed sites of the calcium phosphate compound coating and do not adversely affect on the subsequent antigen-antibody reaction. Therefore, the blocking agent used is not restricted to the limited substances, however, it is preferred that proteins such as casein and albumin are used as a blocking agent.

The thus produced immobilized antigens and immobilized antibodies can be advantageously used as a diagnostic agent utilizing an antigen-antibody reaction in a detection process.

As can be appreciated from the above descriptions, according to the present invention, a diagnostic agent capable of responding to viruses, bacteria and other antigens with a high sensitivity can be easily produced in a simplified method. The diagnostic agent in which particles of the calcium phosphate compound penetrate into the polymeric granules is suitable for use in a liquid specimen, since the coating is not separated from the composite under application of, for example, centrifugal force. Further, since the diagnostic agent of the present invention has a dyed color, observation and evaluation can be easily and exactly accomplished, and also two or more antigen-antibody reactions can be simultaneously observed, if the composites are dyed with different dyes depending upon the types of the antigens.

The present invention will be further described with reference to the following working examples. Note, however, that the present invention should not be restricted to these examples.

EXAMPLE 1

Preparation of polymeric composite 50 g of nylon beads having an average diameter of 5 microns and a density of 1.02 g/cms and 7.5 g of hydroxyapatite particles having a ratio of calcium and phosphorus (Ca/P) of 1.67, average particle diameter of 5 microns, specific surface area of 45 $m^2/g$, an apparent density of 1.8 $g/cm^3$ and a pore size of 500 angstroms were blended at 34 to 47° C. for 5 minutes in the Nara Hybridization System NHS-1 (commercially available from Nara Kikai Seisakusho; rated power: 5.5 kw and rated current: 23 A) and rotated at 8000 rpm to produce nylon beads having a coating of hydroxyapatite applied over a surface of the beads. The hydroxyapatite coating had a thickness of 0.45 microns in average. The resulting nylon composite had an average granule diameter of 5.8 microns, density of 1.12 $g/cm^3$ and pore size of 600 angstroms, and showed a protein adsorption at a level of 3.26 mg of lysozyme per gram.

Figure 2:
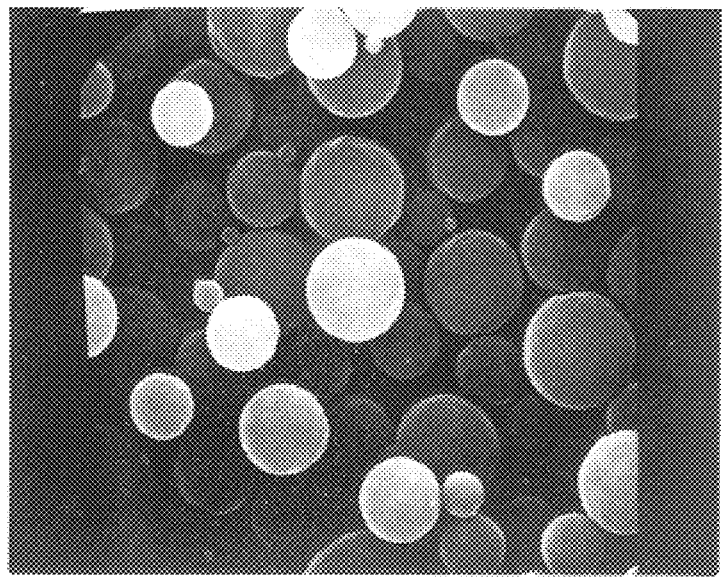
FIG. 2 is a scanning electron micrograph of the nylon beads used in Example 1.
Figure 3:
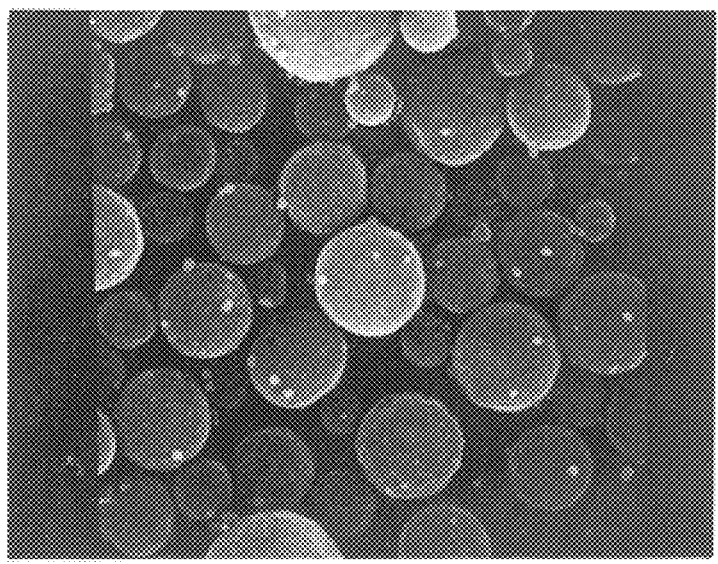
FIG. 3 is a scanning electron micrograph of the polymeric composite obtained in Example 1.

FIG. 2 is a scanning electron micrograph (×1800) showing a granule structure of the nylon beads used in this example, and FIG. 3 is a scanning electron micrograph (×1800) showing a granule structure of the obtained nylon composite.

EXAMPLE 2

Preparation of polymeric composite 50 g of polystyrene beads having an average diameter of 15 microns and a density of 1.04 $g/cm^3$ and 5.0 g of hydroxyapatite particles having a ratio of calcium and phosphorus (Ca/P) of 1.67, a average particle diameter of 20 microns, a specific surface area of 24 $m^2/g$, apparent density of 2.2 $g/cm^3$ and a pore size of 800 angstroms were blended at 36° C. to 64° C. for 5 minutes in the Nara Hybridization System NHS-1 (commercially available from Nara Kikai Seisakusho; rated power: 5.5 kw and rated current: 23 A) and rotated at 8000 rpm to produce polystyrene beads having a coating of hydroxyapatite applied over a surface of the beads. The hydroxyapatite coating had a thickness of 0.22 microns on average. The resulting polystyrene composite had an average granule diameter of 15.4 microns, a density of 1.15 $g/cm^3$ and a pore size of 800 angstroms, and showed a protein adsorption at a level of 1.14 mg of lysozyme per gram.

EXAMPLE 3

Preparation of polymeric composite 400 g of polyethylene beads having an average diameter of 6 microns and a density of 0.92 $g/cm^3$ and 120 g of particles of calcium phosphate compound having a ratio of calcium and phosphorus (Ca/P) of 1.8, an average particle diameter of 80 microns, a specific surface area of 51 $m^2/g$, an apparent density of 1.6 $g/cm^3$ and a pore size of 550 angstroms were blended at 25 to 75° C. for 20 minutes in the hybridization system Hi-x200 (commercially available from Nisshin Engineering; standard blades) and rotated at 4000 rpm to produce polyethylene beads having a coating of calcium phosphate compound applied over a surface of the beads. The coating of calcium phosphate compound had a thickness of 0.82 microns on average. The resulting polyethylene composite had an average granule diameter of 7.44 microns, a density of 1.12 g/cm$^3$ and a pore size of 550 angstroms, and showed a protein adsorption at a level of 4.60 mg of lysozyme per gram.

EXAMPLE 4

Preparation of polymeric composite 50 g of polymethylmethacrylate (PMMA) beads having an average diameter of 7 microns and a density of 1.19 g/cm$^3$ and 5.0 g of particles of calcium phosphate compound having a ratio of calcium and phosphorus (Ca/P) of 1.5, average particle diameter of 2 microns, a specific surface area of 12 m$^2$/g, a apparent density of 2.4 g/cm$^3$ and a pore size of 1000 angstroms were blended at 38° C. to 71° C. for 5 minutes in the Nara Hybridization System NHS-1 (commercially available from Nara Kikai Seisakusho; rated power: 5.5 kw and rated current: 23 A) and rotated at 8000 rpm to produce PMMA beads having a coating of calcium phosphate compound applied over a surface of the beads. The coating of calcium phosphate compound had a thickness of 0.28 microns in average. The resulting PMMA composite had an average granule diameter of 7.5 microns, a density of 1.3 g/cm$^3$ and a pore size of 1000 angstroms, and showed a protein adsorption at a level of 0.32 mg of lysozyme per gram.

COMPARATIVE EXAMPLE 1

This example is intended to explain the case wherein the polymeric composite is not produced.

50 g of polymethylmethacrylate (PMMA) beads having an average diameter of 0.4 microns and a density of 1.19 g/cm$^3$ and 15.0 g of particles of calcium phosphate compound having a ratio of calcium and phosphorus (Ca/P) of 1.67, average particle diameter of 120 microns, specific surface area of 25 m$^2$/g, an apparent density of 2.2 g/cm$^3$ and a pore size of 800 angstroms were blended at 35 to 61° C. for 5 minutes in the Nara Hybridization System NHS-1 (commercially available from Nara Kikai Seisakusho; rated power: 5.5 kw and rated current: 23 A)and rotated at 8000 rpm. However, contrary to the Example 4, no PMMA beads having a coating of calcium phosphate compound applied over a surface of the beads were produced. It was observed that the resultant was only a mixture of the PMMA beads and particles of calcium phosphate compound.

EXAMPLE 5

(1) Preparation of polymeric composite

Nylon beads having an average diameter of 5 microns and a density of 1.03 g/cm$^3$ were dyed with an anthraquinone disperse dye, MITSUI ML Colors ML Red VF-2 (trade name) commercially available from Mitsui Toatsu Senryou Kabushikikaisha. 50 g of the dyed nylon beads and 7.5 g of hydroxyapatite particles having a ratio of calcium and phosphorus (Ca/P) of 1.67, an average particle diameter of 5 microns, a specific surface area of 45 m$^2$/g, an apparent density of 1.8 g/cms and a pore size of 600 angstroms were blended at 32 to 50° C. for 5 minutes in the Nara Hybridization System NHS-1 (commercially available from Nara Kikai Seisakusho; rated power: 5.5 kw and rated current: 23 A) and rotated at 8000 rpm to produce nylon beads having a coating of hydroxyapatite applied over a surface of the beads. The hydroxyapatite coating had a thickness of 0.44 microns in average. The resulting dyed nylon composite had an average granule diameter of 5.8 microns, a density of 1.13 g/cm$^3$ and a pore size of 600 angstroms.

(2) Preparation and evaluation of diagnostic agent 10 ml of a suspension of A-type influenza virus (2000 titers) was added to 0.1 g of the above composite, and the mixture was thoroughly stirred. After stirring, the mixture was centrifuged to remove an excess amount of influenza virus. 10 ml of 0.1% solution of glutaraldehyde was added to the mixture to immobilize the virus adsorbed on the composite. After the virus was immobilized, 5 ml of a blocking agent containing casein, "Block Ace"(trade name) commercially available from Yukijirushi Nyugyou Kabushikikaisha, was added to the virus-immobilized composite and the mixture was thoroughly stirred. The stirred mixture was centrifuged to remove an excess amount of the blocking solution. 10 ml of a physiological type of saline solution was added to the solution to obtain a solution of virus-immobilized composite.

To evaluate the function of the virus-immobilized composite as a virus diagnostic agent, the obtained solution of the virus-immobilized composite was added to a diluted solution of the antiserum of the above influenza virus and antiserums of other viruses. No aggregation image was observed in all the antiserums of the other viruses. Contrary to this, a aggregation image was observed in the antiserum of the above virus, even after the antiserum solution was further diluted to make a volume of 10000 times. These results show that the virus-immobilized composite can act as a virus diagnostic agent having a highly increased sensitivity.

EXAMPLE 6

(1) Preparation of polymeric composite

Polymethylmethacrylate (PMMA) beads having an average granule diameter of 7 microns and a density of 1.19 g/cm$^3$ were dyed with a quinophthalone disperse dye, MITSUI ML Colors ML Yellow VF-2 (trade name) commercially available from Mitsui Toatsu Senryou Kabushikikaisha. 50 g of the dyed PMMA beads and 5.0 g of particles of calcium phosphate compound having a ratio of calcium and phosphorus (Ca/P) of 1.5, average particle diameter of 2 microns, a specific surface area of 12 m$^2$/g, an apparent density of 2.4 g/cm$^3$ and a pore size of 1000 angstroms were blended at 38° C. to 71° C. for 5 minutes in the Nara Hybridization System NHS-1 (commercially available from Nara Kikai Seisakusho; rated power: 5.5 kw and rated current: 23 A)and rotated at 8000 rpm to produce PMMA beads having a coating of calcium phosphate compound applied over a surface of the beads. The coating of calcium phosphate compound had a thickness of 0.27 microns on average. The resulting PMMA composite had an average granule diameter of 7.5 microns, density of 1.3 g/cm$^3$ and a pore size of 1000 angstroms.

(2) Preparation and evaluation of diagnostic agent 10 ml of a suspension of A-type influenza virus (2000 titers) was added to 0.1 g of the above composite, and the mixture was thoroughly stirred. After stirring, the mixture was centrifuged to remove an excess amount of influenza virus. 10 ml of 0.1% solution of glutaraldehyde was added to the mixture to immobilize the virus adsorbed on the composite. After the virus was immobilized, 5 ml of a blocking solution containing casein, "Block Ace"(trade name) commercially available from Yukijirushi Nyugyou Kabushikikaisha, was added to the virus immobilized composite and the mixture was thoroughly stirred. The stirred mixture was centrifuged to remove an excess amount of the blocking solution. 10 ml of a physiological type of saline solution was added to the solution to obtain a solution of virus-immobilized composite.

To evaluate the function of the virus-immobilized composite as a virus diagnostic agent, the obtained solution of the virus-immobilized composite was added to a diluted solution of antiserum of the above influenza virus and antiserums of other viruses. No aggregation image was observed in all the antiserums to other viruses. Contrary to this, an aggregation image was observed in the antiserum of the above virus, even after the antiserum solution was further diluted to make a volume of 8000 times. These results show that the virus-immobilized composite can act as a virus diagnostic agent having a highly increased sensitivity.

EXAMPLE 7

(1) Preparation of polymeric composite 50 g of polystyrene beads having an average diameter of 15 microns and a density of 1.04 g/cm$^3$ and 5.0 g of hydroxyapatite particles having a ratio of calcium and phosphorous (Ca/P) of 1.67, average particle diameter of 20 microns, specific surface area of 24 m$^2$/g, apparent density of 2.2 g/cm$^3$ and pore size of 800 angstroms were blended at 36° C. to 64° C. for 5 minutes in the Nara Hybridization System NHS-1 (commercially available from Nara Kikai Seisakusho; rated power: 5.5 kw and rated current: 23 A) and rotated at 8000 rpm to produce polystyrene beads having a coating of hydroxyapatite applied over a surface of the beads. The hydroxyapatite coating had a thickness of 0.76 microns on average. The resulting polystyrene composite had an average granule diameter of 15.4 microns, a density of 1.15 g/cm$^3$ and a pore size of 800 angstroms. The composite was dyed with an acid dye, Qumasi Brilliant Blue R-250 (solution).

(2) Preparation and evaluation of diagnostic agent 10 ml of a suspension of A-type influenza virus (2000 titers) was added to 0.1 g of the above composite, and the mixture was thoroughly stirred. After stirring, the mixture was centrifuged to remove an excess amount of influenza virus. 10 ml of 0.1% solution of glutaraldehyde was added to the mixture to immobilize the virus adsorbed on the composite. After the virus was immobilized, 5 ml of a blocking solution containing casein, "Block Ace"(trade name) commercially available from Yukijirushi Nyugyou Kabushikikaisha, was added to the virus-immobilized composite and the mixture was thoroughly stirred. The stirred mixture was centrifuged to remove an excess amount of the blocking solution. 10 ml of a physiological type of saline solution was added to the solution to obtain a solution of virus-immobilized composite.

To evaluate the function of the virus-immobilized composite as a virus diagnostic agent, the obtained solution of the virus-immobilized composite was added to a diluted solution of antiserum of the above influenza virus and antiserums of other viruses. No aggregation image was observed in all the antiserums of the other viruses. Contrary to this, an aggregation image was observed in the antiserum to the above virus, even after the antiserum solution was further diluted to make a volume of 8000 times. These results show that the virus-immobilized composite can act as a virus diagnostic agent having a highly increased sensitivity.

We claim:

1. A process for the production of a granular polymer composite which comprises:

physically impinging calcium phosphate compound particles against polymeric granules, said polymeric granules including a surface, to thereby form a coating of said calcium phosphate compound particles on the surface of said polymeric granules, in addition to penetrating at least a part of said particles of said calcium phosphate compound particles into said polymeric granules, said calcium phosphate compound particles having an apparent density of 1.5 to 2.5 g/cm$^3$, and an average particle diameter of not more than 100 microns; said polymeric granules having an average granule diameter of 1 to 20 microns; and said calcium phosphate compound particles have a larger average diameter in comparison to that of the polymeric granules.

2. The process according to claim 1, in which said polymeric granules are granules of a thermoplastic or thermosetting resin having a density of 0.9 to 1.2 g/cm$^3$.

3. The process according to claim 1, in which said polymeric granules have a range of a grain size distribution of $d_{75}/d_{25} \leqq 2$.

4. The process according to claim 1, in which said calcium phosphate compound particles have a ratio of calcium to phosphorus (Ca/P) of 1.0 to 2.0.

5. The process according to claim 1, in which said calcium phosphate compound particles are porous particles of agglomerated primary particles having a specific surface area of not less than 10 m$^2$/g and pore size of 500 to 1000 angstroms.

6. The process according to claim 1, in which said coating has a layer thickness of 0.1 to 5.0 microns.

7. A granular polymer composite produced by the process of claim 1.

8. A granular polymer composite produced by the process of claim 2.

9. A granular polymer composite produced by the process of claim 3.

10. A granular polymer composite produced by the process of claim 4.

11. A granular polymer composite produced by the process of claim 5.

12. A granular polymer composite produced by the process of claim 6.

* * * * *